United States Patent [19]

Matsui et al.

[11] Patent Number: 5,126,262
[45] Date of Patent: Jun. 30, 1992

[54] MONOCLONAL ANTIBODY

[75] Inventors: Masashi Matsui, Osaka, Japan; Soldano Ferrone, Scarsdale, N.Y.

[73] Assignee: Suntory Limited, Osaka, Japan

[21] Appl. No.: 657,253

[22] Filed: Feb. 15, 1991

Related U.S. Application Data

[63] Continuation of Ser. No. 251,980, Sep. 28, 1988, abandoned, which is a continuation of Ser. No. 684,262, Dec. 20, 1984, abandoned.

[51] Int. Cl.$^5$ .................. C12N 5/20; C07K 15/28
[52] U.S. Cl. .................. 530/388.85; 435/70.21; 435/172.2; 435/240.27; 424/85.8; 935/104; 935/107
[58] Field of Search ............... 424/85.8, 88; 530/387, 530/388; 435/70.21, 172.2, 240.27, 7.2, 7.23, 7.91, 7.92, 7.93

[56] References Cited

U.S. PATENT DOCUMENTS 4,522,918  6/1985  Schlom et al. .................. 436/548

FOREIGN PATENT DOCUMENTS 0114670  8/1984  European Pat. Off. .
0154550  9/1985  European Pat. Off. .

OTHER PUBLICATIONS

Chemical Abstracts, vol. 101, No. 21, Nov. 19, 1984, p. 560; "Detection and Enhancement (By Recombinant Interferon) of Carcinoma Cell Surface Antigens Using Monoclonal Antibodies".
Chemical Abstracts, vol. 99, No. 15, Oct. 10, 1983, p. 493; "Differential Regulation of HLA-DR mRNAs and Cell Surface Antigens by Interferon".
Giacomini et al.; The Journal of Immunology, vol. 133, No. 3, Sep., 1984; pp. 1649-1655; "Modulation by Recombinant DNA Leukocyte ($\alpha$) and Fibroblast ($\beta$) Interferons of the Expression and Shedding of HLA- and Tumor-Associated Antigens by Human Melanoma Cells".
Koch et al.; The Journal of Immunology, vol. 132, No. 3, Mar. 1984; pp. 1361-1369; "Ia Antigens and Associated Invariant Chain are Induced Simultaneously in Lines of T-Dependent Mast Cells by Recombinant Interferon-$\gamma^1$".
Chemical Abstracts; vol. 101, No. 13, Sep. 24, 1984, p. 484; "Enhanced Expression of Surface Tumor-Associated Antigens on Human Breast and Colon Tumor Cells After Recombinant Human Leukocyte$\alpha$Interferon Treatment".
Wilson et al.; Int. J. Cancer, vol. 28, 1981, pp. 293-300; Distribution and Molecular Characterization of a Cell-Surface and a Cytoplasmic Antigen Detectable in Human Melanoma Cells with Monoclonal Antibodies.
Khan et al., Cancer Res. 43, 1983, pp. 5868-5872.
Bumol et al., Hybridoma 1(3) 1982, pp. 283-292.
Steplewski, Transplantation Proc. XII, 1980, pp. 384-387.
Morgan et al. Cancer Res. 43, 1983, pp. 3155-3159.
Herlyn et al., Cancer Investigation 1(3), 1983, pp. 215-224.
Dippold et al., PNAS 77, 1980, pp. 6114-6118.
Greiner et al., Cancer Res. 44, 1984, pp. 3208-3214.
Reisfeld, Nature 298, 1982, p. 325.
Eisinger et al., PNAS 79, 1982, pp. 2018-2022.
Ueda et al., "Cell surface antigens of human renal cancer ... MBB", PNAS, vol. 78(8), 1981, pp. 5122-5126.
Cairncross et al., "Cell surface antigens of human astrocytoma ... MAB", PNAS, vol. 79, 1982, pp. 5641-5645.
Imai et al., "Differential effect of IFN on expression of tumor associated antigen ... cells", J. Immunol., vol. 127(2), 1981, pp. 505-508.

(List continued on next page.)

Primary Examiner—John Doll
Assistant Examiner—Robert D. Budens
Attorney, Agent, or Firm—Cushman, Darby & Cushman

[57] ABSTRACT

Specific antibody of the invention is capable of differentiating between malignant and benign tumors, and is obtained by culturing hybridoma cells prepared from tumor cells treated with a certain anti-tumor substance.

4 Claims, 1 Drawing Sheet

OTHER PUBLICATIONS

Liao et al., "Effect of Glutaraldehyde treatment on human melanoma cells . . . antigens", *Cancer Immunol. Immunother.*, 1981, vol. 11, pp. 23-29.

Proc. Natl. Acad. Sci. U.S., vol. 75, pp. 3405-3409, 6215-6219, 1978.

Proc. Natl. Acad. Sci. U.S., vol. 77, pp. 6114-6118, 1980.

Science, vol. 212, U.S., vol. 212, pp. 53-55, 1981.

Proc. Natl. Acad. Sci., U.S., vol. 79, pp. 3265-3269, 3082-3086, 1982.

Houghton et al.; J. Exp. Med., vol. 156; Dec. 1982, pp. 1755-1766; "Surface Antigens of Melanocytes and Melanomas".

Houghton et al.; J. Exp. Med., vol. 160; Jul. 1984, pp. 255-269; "Surface Antigens of Melanoma and Melanocytes".

Koprowski et al.; Proceedings of the International Symposium on the Impact of Biotechnology on Diagnostics held in Rome, Italy, Apr. 16-18, 1985; "Biotechnology in Diagnostics", pp. 135-146.

Matsui et al., Characterization of a Monoclonal . . . J. of Immunology, (Sep. 15, 1987), vol. 139, pp. 2088-2095.

Natali et al., Human Melanoma . . . , in Cutaneous Melanoma and Precursor Lesions, eds. Reuiter et al. (Martinus Nihjoff Publ., Boston, 1984), pp. 19-37.

REACTIVITY OF CL SERIES SUPERNATANTS WITH γ-IFN TREATED COLO 38

CL203-4 AGAINST UNTREATED COLO38(●) γ IFN(250 U/ml)TREATED COLO38(○)
CL207-14    (▲)    (△)
CL212       (●)    (○)
CL611       (■)    (□)

MONOCLONAL ANTIBODY

This is a continuation of application Ser. No. 07/251,980, filed on Sep. 28, 1988, which was abandoned upon the filing hereof which is Rule 62 continuation of Ser. No. 06/684,262 filed Dec. 20, 1984, now abandoned.

FIELD OF THE INVENTION

The present invention relates to an antibody against a trace level of antigen produced by the cells of a specific hybridoma, as well as a process for producing such antibody. More particularly, the invention relates to a specific antibody that is capable of differentiating between malignant and benign tumors and which is obtained by sensitizing an animal with tumor cells which have been treated with an anti-tumor substance selected from the group consisting of cytokine and lymphokine, extracting the spleen from the animal, fusing the cells of the spleen with hybridoma-producing, infinitely growing cells, cloning the fused cells and finally culturing the cloned hybridoma cell line. The invention also relates to a process for producing such antibody. The antibody of the present invention can be used for clinical purposes such as diagnosis and treatment of human tumor cells or tissues.

PRIOR ART

In 1975, Kohler and Milstein prepared from a hybridoma a monoclonal antibody acting on a specific antigen (the monoclonal antibody is hereunder abbreviated as MoAb), the hybridoma being prepared by fusing mouse myeloma cells with the spleen cells of a mouse immunized with sheep red blood cells. Their experiment provided a basic method for preparing MoAb (see Nature, 256: 495-497, 1975). Following the study of Kohler and Milstein, many researchers made attempts at preparing various types of MoAb.

Two major advantages of the method for preparing MoAb by the fusion of cells are the absence of the need for purifying the target antigen and the possibility of producing a homogeneous antibody (MoAb) in large quantities. Because of these advantages, the potential importance of MoAb will not be limited to basic research work; it is expected to provide an effective tool in clinical fields (e.g. diagnosis and treatment of cancers and other intractable diseases) by producing antibodies specific to malignant tumors. Particularly active efforts are being made in the field of tumor immunology wherein researchers are using the cell fusion technique to prepare a wide variety of MoAbs having specificity for tumor cells such as melanoma, colon cancer, and leukemic cells (see Proc. Natl. Acad. Sci. US. 75: 3405-3409, 1978, ibid. 76: 2927-2931, 1979, ibid. 77: 6114-6118, 1980, ibid. 76: 1438-1442, 1979, Curr. Top. Microbiol. Immunol. 81: 164-169, 1978).

However, most of the MoAbs developed so far are cross-reacting and recognize not only the target malignant tumor cells but also other cells such as benign tumor cells. Therefore, these MoAbs may show "false positiveness" when used in clinical applications such as diagnosis and treatment of malignant tumors. In order to avoid this problem, it is necessary to prepare an antibody against an antigen which is specific only for the target malignant tumor cells. Several types of cancer have been found to contain tumor-associated antigens such as melanoma associated antigen (MAA), $\alpha$-feto protein (AFP), carcino embryonic antigen (CEA) and spleen cancer associated antigen (Science, 212: 53-55, 1981), and attempts are being made to prepare MoAbs against these antigens. One of the most advanced fields is the analysis of antigens in melanoma, and clinical studies are being made on the MoAbs against these antigens (see Melanoma-Antigens and Antibodies, ed. R. A. Reisfeld and S. Ferrone, Plenum Press, N.Y., 1982), but no MoAb has been obtained that is completely free from cross-reaction with benign tumors such as melanocytes.

Usually, malignant tumor cells contain a very small amount of a specific antigen and the level of their antigenicity is so low that it is difficult to obtain an antibody against this specific antigen by directly immunizing an animal with these tumor cells. In an attempt to obtain antibodies having specific reactivity, tumor cells with which to immunize animals were treated with formalin or irradiated with UV radiation or X-rays so that the antigenicity of the tumor-specific antigen is sufficiently increased to obtain the desired MoAb (see Melanoma-Antigens and Antibodies, ed. R. A. Reisfeld and S. Ferrone, Plenum Press, N.Y., 1982), but no satisfactory results have been obtained by this approach.

As a result of various studies conducted with a view to solving these problems, the present inventors have found that by treating tumor cells with an anti-tumor cytokine or lymphokine, preferably gamma-interferon (hereunder abbreviated as INF-$\gamma$) before they are used to immunize an animal, the antigenicity of a previously unknown antigen that is present in a trace level and which is specific to those tumor cells can be increased to such a degree that an antibody specific to that antigen can be produced in the animal. The inventors have also found that an antibody capable of differentiating between malignant and benign tumors can be prepared from said antigen. These findings have led to the accomplishment of the present invention.

Interferons (hereunder abbreviated as IFN) are known to have several biological functions such as anti-viral activity, inhibition of cell growth and anti-tumor activity. It is also known that some interferons increase the antigenicity of some common tissue-compatible antigens in an in vitro system, such as human leukocyte antigen (HLA), $\beta_{82}$-microglobulin and melanoma associated antigen (MAA). While many reports have been published to show that $\alpha$- and $\beta$-IFNs increase the antigenicity of Class I antigens (e.g. HLA-A and -B) in certain types of cells (see Proc. Natl. Acad. Sci. US. 75: 6215-6219, 1978, ibid. 79: 3265-3269, 1982, ibid. 79: 3082-3086, 1982 and Eurp. J. Immunol. 9: 446-449, 1979), no report has been published as to whether IFN-$\gamma$ has a similar activity.

SUMMARY OF THE INVENTION

In the course of the studies that led to the accomplishment of the present invention, the inventors treated malignant melanoma cells with IFN-$\gamma$ and sensitized a mouse with the treated cells. Spleen cells isolated from the sensitized mouse were then fused with mouse myeloma cells, and the fused cells were cloned to obtain hybridomas. The hybridomas were found to be capable of producing antibodies having an unusually high specific reactivity. A probable reason for the production of such highly specific antibodies would be that the direct anti-tumor activity of IFN-$\gamma$ causes a certain change in the treated tumor cells to exhibit antibody-producing stimulation, and the animal sensitized with these tumor cells produced a sufficient amount of specific antibody. Therefore, it is expected that substances other than IFN-γ that have direct anti-tumor activity such as lymphokine (e.g. lymphotoxin, LT) and cytokine (e.g. tumor necreosis factor, TNF) would be useful in inducing tumor-specific antigens. It is also expected that by treating tumor cells other than melanoma cells with lymphokine or cytokine, previously undiscovered antigens can be induced, and useful antibodies against the induced antigens, such as one that reacts specifically with the target tumor cells, can be created by the cell fusion technique.

DETAILED DESCRIPTION OF THE INVENTION

Figure 1:
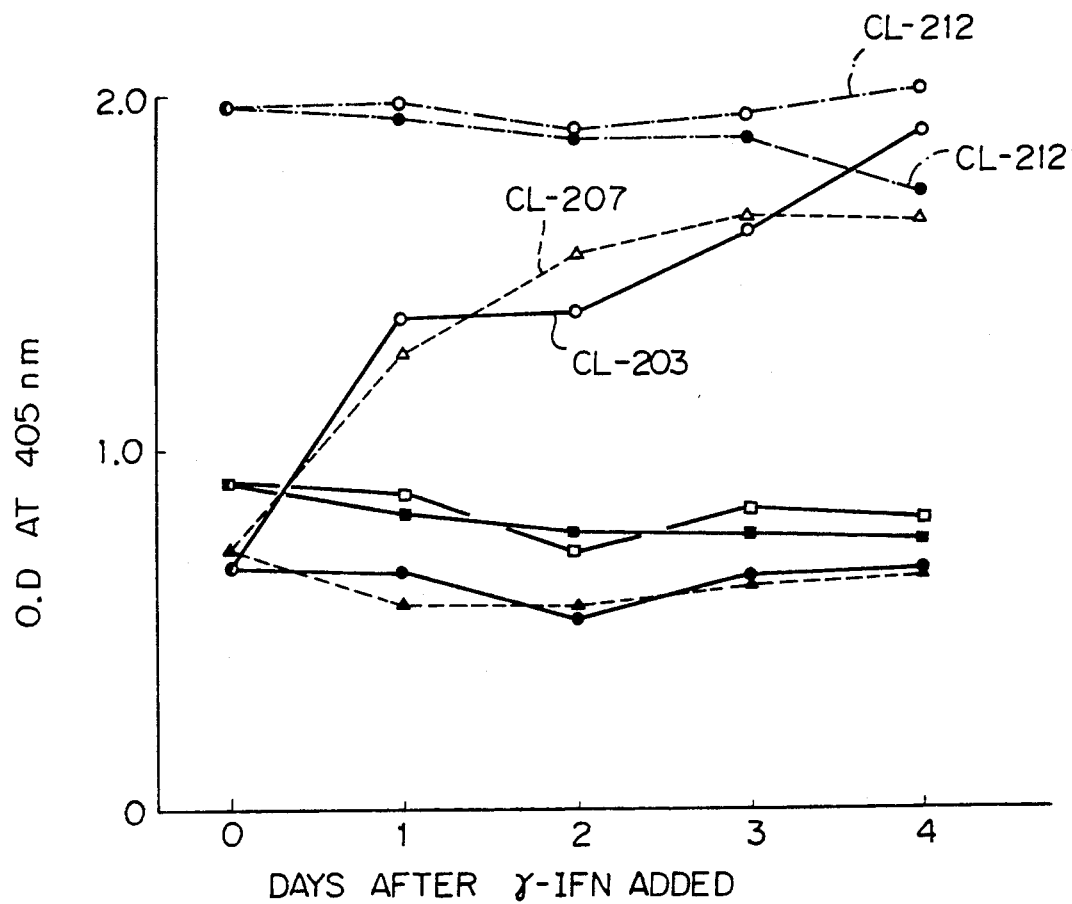
FIG. 1 shows the analysis of the antigen induced by IFN-γ treatment.

The first stage of preparing the novel monoclonal antibody is to treat tumor cells such as melanoma cells Colo 38 with cytokine or lymphokine, preferably with IFN-γ (e.g. IFN-γ produced by $E.\ coli$ created by recombinant DNA technology). The concentration of the treating agent and the duration of the treatment of the tumor cells are such that they do not inhibit, or inhibit only slightly, the viability of the tumor cells but are sufficient to cause a certain stimulation in said cells. Suitable levels of concentration and duration of treatment may be determined empirically by those skilled in the art for each case. As guide FIGURE, melanoma cells Colo 38 may be treated with 250-500U/ml of IFN-γ for a period up to 96 hours, preferably about 72 hours. Other treatment conditions such as temperature and pH may be those which are conventionally used in cell cultivation.

In the next stage, the tumor cells treated under the conditions shown above are used to sensitize an animal by a standard method. Spleen cells are isolated from the immunized animal and are fused with hybridoma-producing, infinitely growing cells. The fused cells are cloned to obtain a hybridoma that produces a monoclonal antibody that recognizes specifically the target malignant tumor. The sequence of this hybridoma production is already known and may comprise the following steps. About $5 \times 10^6$ treated tumor cells are suspended in 0.2 ml of PBS (phosphate-buffered saline) and the suspension is injected into the abdominal cavity of a BALB/c mouse several times (preferably three times) at intervals of 7 to 10 days, thereby immunizing the animal. About three days after the final immunization, spleen cells extracted from the mouse are fused with mouse myeloma cells with the aid of a fusing agent such as polyethylene glycol. The hybridoma is selectively cultured in a HAT medium (RPMI 1640+10% serum; with hypoxanthine, aminopterin and thymidine) by a conventional method, and the supernatant of the culture is subjected to primary screening by the ELISA (enzyme-linked-immunosorbent assay) method for its reactivity with the target cells. The hybridoma found positive in the primary screening is preferably sub-cloned by the limited dilution method to form a monoclone.

The sub-class of the monoclonal antibodies produced by the cloned hybridoma may be identified by an immunological technique. A commercial mouse globulin identifying kit may be conveniently used to identify the sub-class of mouse-derived MoAbs. Analysis of the antigen corresponding to the antibody of the present invention is performed by the following procedure: the solubilized protein from tumor cells labelled with a radioisotope is reacted with the antibody, and the antigen bound with said antibody is dissociated with β-mercaptoethanol, and subsequently subjected to SDS polyacrylamide gel electrophoresis (SDS PAGE). The reactivity of the antibody with the tissue of the target tumor may be examined by first fixing the extracted tumor tissue with acetone, staining the fixed tissue by the ELISA method, and observing the stained tissue under a microscope.

As shown above, the essence of the present invention is to use a substance having direct anti-tumor activity such as lymphokine, cytokine, or, preferably, INF-γ in preparing an antibody that recognizes a tumor-specific antigen which has been induced in an amount sufficient to exhibit antibody-producing stimulation. The so prepared antibody reacts only with the desired malignant tumor cells and recognizes benign cells almost negligibly. It is also possible to obtain by the present invention an antibody that is highly reactive with the tissue of a malignant tumor extracted from the patient, as well as with the INF-γ treated tumor cells used as the antigen, and untreated tumor cells.

In the current diagnosis of cancer diseases, especially melanoma diseases, malignant tumors are distinguished from being tumors exclusively by experienced doctors. As will be readily understood to those skilled in the art, any paramedical technician having ordinary knowledge can easily distinguish malignant tumors with the aid of the antibody of the present invention. This will therefore provide an effective tool in the treatment of cancer diseases.

The advantages of the present invention will become more apparent by reading the following working examples, to which the scope of the invention is by no means limited. It should be understood that the process of antibody production according to the present invention is not limited to the preparation of an antibody specific to melanoma cells as illustrated in the following examples but that said process is also applicable to the production of antibodies specific to other malignant tumor cells.

EXAMPLE

1) Treating melanoma cells Colo 38 with IFN-γ

Cultured melanoma cells Colo 38 ($1 \times 10^5$ cells/ml), as well as human IFN-γ (250U/ml and 500U/ml) isolated from transformed $E.\ coli$ cells that were constructed by recombinant DNA technology, were cultivated in a medium ( containing 10% calf serum and gentamicin, 1 μg/ml) for 96 hours at 37° C. As a control, the same melanoma cells were cultured under the same conditions except that no IFN-γ was present. At 24-hr intervals, the number of living cells in each culture was counted by staining with Trypan Blue. A similar experiment was conducted using a higher concentration of Colo 38 ($6 \times 10^5$ cells/ml) and a period of 72 hours. When the initial concentration of Colo 38 was $1 \times 10^5$ cells/ml, the cell growth was inhibited by the presence of IFN-γ (cell number was about 60% of the untreated cells after 72-hr culture in the presence of 250 U/ml of IFN-γ), but no morphological changes were observed in the cells under a microscope. When the initial concentration of Colo 38 was increased to $6 \times 10^5$ cells/ml, the percent survival was kept about 80% in the presence of 250 U/ml of IFN-γ but a gradual decrease with time was observed at the concentration of 500 U/ml.

Since the purpose of treating melanoma cells with IFN-γ was to inhibit their growth and cause a certain stimulation of the membrane on the cell surface while maintaining their survival as high as possible, the following experiments were conducted by using 250U/ml of IFN-γ and limiting the duration of IFN-γ treatment to 72 hr.

2) Immunization of mouse and hybridoma preparation

Melanoma cells (Colo 38, $10^5$ cells/ml) were cultured at 37° C. for 72 hours in RPMI-1640 medium (with 10% calf serum and 1 μg/ml gentamycin) containing 250U/ml of human IFN-γ that was prepared by DNA recombinant technology. The cells were collected by centrifuge. After washing with PBS (phosphate buffered saline), $5 \times 10^6$ cells were suspended in 0.2 ml of PBS, and the suspension was injected into the abdominal cavity of a BALB/c mouse three times at intervals of 10 days.

Three days after the final immunization, the spleen was extracted aseptically from the mouse and dispersed into individual cells, which were then washed twice with serum free RPMI-1460. The number of spleen cells that could be extracted from one mouse was in the range of $1.2-1.4 \times 10^8$. The spleen cells were fused with $2 \times 10^7$ mouse myeloma cells (P3×63 Ag8 - 653) by treatment in RPMI-1640 containing 40% polyethylene glycol 1000 for 5 minutes. After washing with RPMI-1640 containing 10% calf serum, the fused cells were suspended to give a concentration of $5 \times 10^5$ myeloma cells per ml, and the suspension was incubated for 24 hours in the presence of 5% $CO_2$. The culture medium was replaced by a HAT medium (RPMI-1640 containing 10% calf serum, $10^{-4}$M hypoxanthine, $4 \times 10^{-7}$M aminopterin and $1.6 \times 10^{-5}$M thymidine), and the culture was continued on a microplate having 96 wells. Ten days later, the culture was transferred into an aminopterin-free HAT medium (HT medium), and the culture was continued for an additional 14-21 days. The supernatant of the cell culture obtained was subjected to primary hybridoma screening by the ELISA method.

3) Hybridoma screening and cloning 3-1) Screening by the ELISA method

Colo 38 cells treated with IFN-γ and those untreated with IFN-γ were used as the target cells. A cell suspension containing $10^5$ target cells in 50 μl of PBS and 50 μl of the culture supernatant of the hybridoma were incubated at 4° C. for 1 hour. Thereafter, the unadsorbed antibodies were washed away with Hanks solution containing 1% BSA (bovine serum albumin). The culture was reacted for 30 minutes with a secondary antibody which was a peroxidase labelled sheep anti-mouse antibody (product of Cappel Inc.) and washed with PBS. The color development of o-phenylenediamine was analyzed by a multiscanner (product of Titertech Inc.) at 405 nm. The results were estimated based on the measured absorbancy as follows: 0-0.3 (−), 0.3-0.5 (±), 0.5-1.0 (+) and >1.0 (++).

The 168 clones obtained by the HAT selection in 2) were checked for their reactivity with IFN-γ treated Colo 38 and with untreated Colo 38; whereby 34 clones had absorbance values of 0.3 or more. In order to check for the existence of anti-HLA antibody, 9 out of the 34 clones were subjected to the ELISA method with a view to determining their cross-reactivity with LG-2 cells of Burkitt's lymphoma B treated with IFN-γ and those untreated with IFN-Y (the LG-2 cells are positive to HLA-A, B and HLA-$D_R$). Five out of the nine clones tested were reactive with LG-2 irrespective of their treatment with IFN-γ. The remaining four clones produced antibodies that did not react with LG-2 but reacted with Colo 38.

3-2) Screening by histological method

The clones selected in 3-1) were checked for their reactivity with tissue specimens. Melanoma tissues obtained by biopsy or surgical operation were sliced to a 4-μm thick section which was fixed with acetone and overlaid with the supernatant of the culture of a test clone. The specimen was left to stand for 30 minutes at room temperature. The specimen was washed with cooled PBS for 5 minutes and reacted with peroxidase labelled anti-mouse serum for 30 minutes. The unreacted mouse serum was washed with cold PBS, then with hydrogen peroxide (0.1-1%). The degree of brown staining of the sample was examined under a microscope.

The supernatant of the culture of 34 clones that were found positive in 3-1) were also checked for their reactivity with melanoma tissues by the same procedure. The results were as follows: two clones (CL-208 and CL-308) were extremely reactive; five clones (CL-203, CL-207 and three others) were strongly reactive; and ten clones had moderate reactivity. Although the correlation between the reactivity with cultured Colo 38 cells and that with the extracted tissues was not clear enough, the clones that strongly reacted with the culture of IFN-γ treated Colo 38 cells had a tendency to strongly react with the extracted tissues also.

It is interesting to note that the supernatants of the culture of two clones (CL-203 and CL-207) that exhibited strong reactivity both with cultured Colo 38 cells and with extracted tissues did not react with a benign tumor (melanocyte), and their reactivity with LG-2 cells was almost negligible. This indicates that the antibody produced by the clones (hybridomas) designated CL-203 and CL-207 are useful not only in distinguishing a malignant tumor (melanoma) from a benign tumor (melanocyte) but also in treating melanoma diseases. CL207 SBM296 was deposited at the Fermentation Research Institute, 1-3, Higashil 1-chrome, Tsukubashi, Ibaraki-Ken, 305 Japan, on Nov. 10, 1987. The deposit has been accorded accession No. FERM BP-1567.

3-3) Preparation of monoclonal hybridoma

The positive clones selected in 3-1) and 3-2) were subcloned to monoclonal antibodies by the limited dilution method in the following manner. The hybridoma was diluted to give a concentration of not more than 10 cells per ml, and the dilution was distributed among 96 wells in a microplate so that each well contained 0.1 ml of the dilution. The microplate was subjected to incubation in HAT medium.

As feeder layer cells, $2 \times 10^5$ ml of spleen cells of BALB/c mice were used.

4) Antigen analysis

The types of antigens that could be recognized by the antibodies produced from several clones of the hybridoma prepared in 3) were determined both by the immunological precipitation method and by examining the clones' reactivity with Colo 38 cells being cultured in the presence of IFN-γ.

5 4-1) Analysis by the immuno-precipitation method

Cultured Colo 38 cells whose protein had been labelled with $^{35}$S-methionine were collected and the protein that solubilized with a surfactant (Renex 30) was used as an antigen. The supernatant of a cultured hybridoma (50 μl) was reacted at 4° C. for 30 minutes with protein A-cephalose CL4B (50 μl, Pharmacia Labs., Inc.) to which rabbit anti-mouse antibody had been bound. To the reaction mixture, 10 μl of the 35S-methionine-labelled antigen was added. The resulting mixture was left to stand for 60 minutes, then washed five times with PBS by centrifuge. The finally obtained complex (precipitate) was boiled for 2 minutes in 100 μl of 1% SDS containing 1 mM β-mercaptoethanol. Thereafter, the mixture was subjected to 3-15% SDS-PAGE (SDS-polyacrylamide gel electrophoresis) to analyze the occurrence of protein bands labelled with $^{35}$S-methionine.

The clones of the present invention, i.e., CL-203 and CL-207, as well as their respective subclones CL-203-4 and CL-207-14, which produced antibodies reacting with melanoma but not with a benign tumor (melanocyte), had protein bands at about 100 kd. On the other hand, CL-208 and CL-306, which produced antibodies outside the scope of the present invention and which reacted strongly not only with melanoma cells and tissues but also with the benign melanocyte, had protein bands at ca. 44 kd and ca. 12 kd, respectively. It is therefore clear that the antibodies according to the present invention recognize specific antigens that differ from those produced by CL-208 and CL-306.

The immunoglobulin subclass of the antibody produced by CL-203 and CL-207 was identified as IgGl, using a mouse immunolobulin subtype identification kit (product of Boehringer Mannheim Biochemicals, Indianapolis, U.S.A.).

4-2) Analysis of reactivity with antigens induced by IFN-γ treatment

A check was made as to whether the antibodies produced by CL-203 and CL-207, as well as by their subclones CL-203-4 and CL-207-14, could recognize specifically the antigens induced in IFN-γ treated Colo 38 cells. Colo 38 cells were incubated for 4 days in RPMI-1640 medium (containing 10% calf serum) containing 250U/ml of IFN-γ and in IFN-γ free RPMI-1640 medium. The change in the amounts of the antigens recognized by the antibodies produced by CL-203 and CL-207 was measured by the ELISA method. The same experiment was conducted with two other clones, i.e., CL-212 as prepared in this Example which produces an antibody outside the scope of the present invention which recognizes Colo 38 cells strongly, and CL-611, also prepared in this Example, which recognizes Colo 38 cells moderately. The results are shown in FIG. 1, from which one can see that the amount of the antigen recognized by the antigens from CL-203 and CL-207 that were induced in IFN-γ treated Colo 38 cells increased with incubation time whereas no change was observed in the amount of the antigen recognized by the antigens produced from CL-212 and CL-611. This shows that, as a result of the treatment with IFN-γ, antigens were induced in sufficient amounts to exhibit strong antigenicity. It can be concluded that CL-203 and CL-207 are clones that produce antibodies against the so induced antigens.

The foregoing description was made referring only to the antibody produced by hybridoma cells. However, in a practical application of the present invention, a malignant tumor specific antigen induced in tumor cells such as melanoma that have been treated with an anti-tumor substance such as gamma interferon can be isolated, purified, and administered to an animal, whereupon an antibody specific to the malignant tumor will be produced in vivo. The antibody obtained from this animal can be used in the diagnosis or treatment of malignant tumors as effectively as the antibody produced by hybridoma cells according to the present invention.

What is claimed is:

1. A hybridoma cell line having all the identifying characteristics of the hybridoma cell line having F.R.I. Accession No. FERM BP-1567, wherein said hybridoma cell line produces a monoclonal antibody which immunologically binds an antigen of about 100 kD which is induced or enhanced on the surface of Colo 38 melanoma cells, said melanoma cells having been previously contacted with gamma interferon, and said antibody being non-reactive with any other antigens existing in Colo 38 melanoma cells.

2. The hybridoma cell line of claim 1 having F.R.I. Accession No. FERM BP-1567.

3. A monoclonal antibody produced by the hybridoma of claim 1.

4. A monoclonal antibody produced by the hybridoma of claim 2.